(12) United States Patent
Johnsen et al.

(10) Patent No.: US 8,834,855 B2
(45) Date of Patent: Sep. 16, 2014

(54) SUNSCREEN COMPOSITIONS COMPRISING CAROTENOIDS

(75) Inventors: Geir Johnsen, Trondheim (NO); Per Age Lysaa, Oslo (NO); Kristin Aamodt, Oslo (NO)

(73) Assignee: Promar AS (NO)

( * ) Notice: Subject to any disclaimer, the term of this patent is extended or adjusted under 35 U.S.C. 154(b) by 1255 days.

(21) Appl. No.: 11/795,668

(22) PCT Filed: Jan. 23, 2006

(86) PCT No.: PCT/GB2006/000220
§ 371 (c)(1),
(2), (4) Date: Apr. 15, 2008

(87) PCT Pub. No.: WO2006/077433
PCT Pub. Date: Jul. 27, 2006

(65) Prior Publication Data
US 2008/0260662 A1    Oct. 23, 2008

(30) Foreign Application Priority Data
Jan. 21, 2005 (GB) .................................. 0501365.1

(51) Int. Cl.
| A61K 8/34 | (2006.01) |
| A61Q 17/04 | (2006.01) |
| A61K 8/49 | (2006.01) |
| C07C 29/74 | (2006.01) |
| C07D 301/32 | (2006.01) |

(52) U.S. Cl.
USPC ............. 424/59; 424/70.9; 568/825; 549/541

(58) Field of Classification Search
USPC ...................... 424/59, 70.9; 568/825; 549/541
See application file for complete search history.

(56) References Cited

U.S. PATENT DOCUMENTS

| 4,699,781 A | 10/1987 | Goupil |
| 5,210,186 A | 5/1993 | Mikalsen et al. |
| 5,308,759 A | 5/1994 | Gierhart |
| 5,352,793 A | 10/1994 | Bird et al. |
| 5,382,714 A | 1/1995 | Khachik |
| 5,648,564 A | 7/1997 | Ausich et al. |
| 5,654,488 A | 8/1997 | Krause et al. |
| 5,705,146 A | 1/1998 | Lindquist |

(Continued)

FOREIGN PATENT DOCUMENTS

| CA | 1310969 | 12/1992 |
| CA | 2177752 | 12/1996 |

(Continued)

OTHER PUBLICATIONS

"A UV absorbing compound in HPLC pigment chromatograms obtained from Iceland Basin Phytoplankton", Liewellyn et al., Marine Ecology Progress Series, vol. 158,:283-287, 1997.*

(Continued)

*Primary Examiner* — Ernst V Arnold
*Assistant Examiner* — Hong Yu
(74) *Attorney, Agent, or Firm* — Schwegman Lundberg & Woessner, P.A.

(57) ABSTRACT

The invention concerns methods of treating or preventing the effects of irradiation in a human or non-human animal using carotenoid compounds, preferably diadinoxanthin, diatoxanthin and/or fucoxanthin as well as photoprotective compositions and their use to prepare photoprotective or photoprotected products.

21 Claims, 4 Drawing Sheets

(56) References Cited

U.S. PATENT DOCUMENTS

| | | | |
|---|---|---|---|
| 5,712,311 A | 1/1998 | Soudant et al. | |
| 5,744,502 A | 4/1998 | Lignell et al. | |
| 5,753,209 A | 5/1998 | Ascione et al. | |
| 5,780,301 A | 7/1998 | Saito et al. | |
| 5,824,312 A | 10/1998 | Unger et al. | |
| 5,827,508 A | 10/1998 | Tanner et al. | |
| 5,828,312 A | 10/1998 | Yamazaki | |
| 5,876,782 A | 3/1999 | Sas et al. | |
| 5,951,968 A | 9/1999 | Forestier et al. | |
| 5,965,795 A | 10/1999 | Hirschberg et al. | |
| 6,000,551 A | 12/1999 | Kanel et al. | |
| 6,015,684 A | 1/2000 | Jacobson et al. | |
| 6,022,701 A | 2/2000 | Boussiba et al. | |
| 6,084,118 A | 7/2000 | Lindquist | |
| 6,103,940 A | 8/2000 | Paust et al. | |
| 6,132,790 A | 10/2000 | Schlipalius | |
| 6,169,217 B1 | 1/2001 | Cheryan | |
| 6,254,898 B1 | 7/2001 | Bragaglia | |
| 6,296,877 B1 | 10/2001 | Auweter et al. | |
| 6,316,012 B1 | 11/2001 | N'Guyen et al. | |
| 6,376,717 B2 | 4/2002 | Schloemer et al. | |
| 6,399,105 B1 | 6/2002 | Collin | |
| 6,433,025 B1 | 8/2002 | Lorenz | |
| 6,500,869 B1 | 12/2002 | Driller | |
| RE38,009 E | 2/2003 | Garnett et al. | |
| 6,540,654 B2 | 4/2003 | Levy et al. | |
| 6,579,714 B1 | 6/2003 | Hirabayashi et al. | |
| 6,610,867 B2 | 8/2003 | Jakel et al. | |
| 6,627,795 B1 | 9/2003 | Coughlan et al. | |
| 6,639,113 B2 | 10/2003 | Runge et al. | |
| 6,669,944 B2 | 12/2003 | Bharathi | |
| 6,677,134 B2 | 1/2004 | Pasamontes et al. | |
| 6,689,400 B2 | 2/2004 | Majeed | |
| 6,706,278 B1 | 3/2004 | Tsubokura et al. | |
| 6,743,953 B2 | 6/2004 | Kumar et al. | |
| 6,773,708 B1 | 8/2004 | Lignell et al. | |
| 6,787,147 B1* | 9/2004 | Huner et al. | 424/401 |
| 7,220,417 B2 | 5/2007 | Nizard et al. | |
| 2003/0003528 A1 | 1/2003 | Brzostowicz et al. | |
| 2003/0206972 A1 | 11/2003 | Babish et al. | |
| 2003/0232892 A1 | 12/2003 | Guerra-Santos et al. | |
| 2004/0018279 A1 | 1/2004 | Johnson et al. | |
| 2004/0022881 A1 | 2/2004 | Hauptmann et al. | |
| 2004/0024264 A1 | 2/2004 | Ernst et al. | |
| 2004/0078846 A1 | 4/2004 | Desouza et al. | |
| 2004/0081628 A1 | 4/2004 | Gierhart et al. | |
| 2004/0204612 A1 | 10/2004 | Seko et al. | |
| 2004/0253724 A1 | 12/2004 | Yamaoka | |
| 2005/0009788 A1 | 1/2005 | Lockwood et al. | |
| 2005/0009930 A1 | 1/2005 | Lockwood et al. | |
| 2005/0038271 A1 | 2/2005 | Khachik | |
| 2005/0124032 A1 | 6/2005 | De La Fuente Moreno et al. | |
| 2005/0124033 A1 | 6/2005 | Sharpe et al. | |
| 2005/0226858 A1 | 10/2005 | Kitamura et al. | |
| 2005/0228188 A1 | 10/2005 | Sumida et al. | |
| 2006/0247169 A1 | 11/2006 | Matsuzawa et al. | |

FOREIGN PATENT DOCUMENTS

| | | |
|---|---|---|
| CA | 2251457 | 4/2000 |
| CA | 2369800 | 10/2000 |
| CA | 2381822 | 12/2001 |
| CN | 1392244 | 1/2003 |
| CN | 1392251 | 1/2003 |
| DE | 19811692 | 9/1999 |
| DE | 10035512 | 1/2002 |
| EP | 0898955 A2 | 3/1999 |
| EP | 1063959 B1 | 11/2002 |
| EP | 0898955 B1 | 6/2006 |
| FR | 1591570 | 5/1970 |
| FR | 2822701 | 10/2002 |
| JP | 6-062878 | 3/1994 |
| JP | 6-329576 | 11/1994 |
| JP | 7-010736 | 1/1995 |
| JP | 07-101872 A | 4/1995 |
| JP | 7-224029 | 8/1995 |
| JP | 7-224278 | 8/1995 |
| JP | 7-227278 | 8/1995 |
| JP | 11-269175 | 10/1999 |
| JP | 2002-265313 | 9/2002 |
| JP | 2004-035528 | 2/2004 |
| RU | 2054442 C1 | 2/1996 |
| RU | 2158586 | 11/2000 |
| WO | WO-99/03571 A1 | 3/1991 |
| WO | WO-97/16175 A1 | 5/1997 |
| WO | WO-99/47109 A1 | 9/1999 |
| WO | WO-99/62315 A2 | 12/1999 |
| WO | WO-00/24369 A1 | 5/2000 |
| WO | WO-02/12183 A1 | 2/2002 |
| WO | WO-02/064110 A2 | 8/2002 |
| WO | WO-03/033683 A1 | 4/2003 |
| WO | WO-03/105791 A1 | 12/2003 |
| WO | WO-2004/018417 A1 | 3/2004 |
| WO | WO-2004/069186 A2 | 8/2004 |
| WO | WO-2005/032504 A1 | 4/2005 |
| WO | WO-2005/042007 A1 | 5/2005 |

OTHER PUBLICATIONS

"Carotenoids of Tunicate, III. The Structural Elucidation of Two New Marine Carotenoids, Amaroucixanthin A and B", Matsuno et al., Journal of Natural Products, vol. 48, No. 4, p. 606-613, Jul.-Aug. 1985.*

"Diacetylenic caretonoids fro *Euglena viridis*", Fiksdahl et al., Phytochemistry, vol. 27, Issue 5, 1988, p. 1447-1450.*

"Carotenoids synthesis: a progress report", Pfander et al., Pure and Applied Chemistry, vol. 69, No. 10, p. 2047-2060, 1997.*

Dambek et al.: Biosynthesis of fucoxanthin and diadinoxanthin and function of initial pathway genes in *Phaeodactylum tricornutum*, Journal of Experimental Botany, 2012, 63 (15):5607-12.*

Zhang et al.: Applying and comparing two chemometric methods in absorption spectral analysis of photopigments from Arctic microalgae, Journal of Microbiological Methods, 83, 2010, 120-126.*

Mao et al.: The pigmental composition and the absorption spectral analysis of *Ulothrix* sp. and benthic diatoms in the intertidal zone of Great Wall Station, Antarctica, Antarctic Research, 1995, vol. 6, No. 1, 73-78.*

Baumeler et al.: Synthese von (6R, all-E)-Neoxanthin and verwandten Allen-Carotinoiden, Helv. Chim. Acta, 1992, vol. 75, issue 3, 773-790.*

Bjørnland et al.: Carotenoids of the Florida red tide dinoflagellate *Karenia brevis*, Biochemical Systematics and ecology, 31, 2003, 1147-1162.*

Fujiki et al.: Relationship between light absorption and the xanthophyll-cycle pigments in marine diatoms, Plankton Biology and Ecology, 2001, 48(2), 96-103.*

Olaizola et al.: Non-photochemical fluorescence quenching and the diadinoxanthin cycle in a marine diatom, Photosynthesis Research, 1999, 59, 73-80.*

*In: Sunscreens: Development, Evaluation, and Regulatory Aspects*, Lowe, N. J., Editors, Marcel Dekker, Inc.,(1997), 390-397, 411-420, 520 and 521.

"Copper-Peptide and Titanium Dioxide Products Based on Integrity and True Science", [on-line]. [retrieved Dec. 20, 2007]. Retrieved from the Internet: <URL: http://www.suntanscience.com/>, (2007), 23 pgs.

"Structure of Carotenoids", [on-line]. [retrieved Apr. 12, 2007]. Retrieved from the Internet: <URL: http://www.food-info.net/uk/caro/stru.htm>, (2007), 5 pgs.

"The Carotenoids Page", [on-line]. {retrieved Mar. 12, 2007]. Retrieved from the Internet: <URL: http://dcb-carot.unibe.ch/nomen.htm>, (2007), 4 pgs.

PCT Application No. PCT/GB2006/000220, International Search Report mailed Apr. 12, 2006, 8 pgs.

PCT Application No. PCT/GB2006/000220, Written Opinion mailed Apr. 12, 2006, 8 pgs.

(56) References Cited

OTHER PUBLICATIONS

Britton, G., "Structure and Properties of Carotenoids in Relation to Function", *FASEB Journal*, 9(15), (1995), 1551-1558.

Britton G., et al., "Chapter 2—Carotenoids Today and Challenges for the Future", In: *Carotenoids*, vol. 1A: *Isolation and Analysis*, (1995), 13-16.

Diffey, B. L., "In Vitro Assessment of the Broad-Spectrum Ultraviolet Protection of Sunscreen Products", *Journal of the American Academy of Dermatology*, 43(6), (2000), 1024-1035.

Dunford, R., et al., "Chemical Oxidation and DNA Damage Catalysed by Inorganic Sunscreen Ingredients", *FEBS Letters*, 418(1-2), (1997), 87-90.

Gilmore, A. M., "Mechanistic Aspects of Xanthophyll Cycle-Dependent Photoprotection in Higher Plant Chloroplasts and Leaves", *Physiologia Plantarum*, 99(1), (1997), 197-209.

Gröninger, A., et al., "Photoprotective Compounds in Cyanobacteria, Phytoplankton and Macroalgae—A Database", *Journal of Photochemistry and Photobiology B: Biology*, 58(2-3), (2000), 115-122.

Haugen, J. A., et al., "Improved Isolation Procedure for Fucoxanthin", *Phytochemistry*, 28(10), (1989), 2797-2798.

Haugen, J. A., "Studies on Algal Carotenoids—Isolation, Analysis, Chemosystematics, Stereochemistry and Synthesis", Thesis, Organic Chemistry Laboratories, Norwegian Institute of Technology—NTH,(1994), 53 pgs.

Haywood, R., et al., "Sunscreens Inadequately Protect Against Ultraviolet-A-Induced Free Radicals in Skin: Implications for Skin Aging and Melanoma?", *J. Invest. Dermatol.* 121(4) 2003, 862-868.

Ito, M., et al., "Recent Progress in Carotenoid and Retinoid Synthesis", *Pure&Appl. Chem.*, 66(5), (1994), 939-946.

Jeffrey, S. W., et al., "Phytoploankton Pigments in Oceanography: Guidelines to Modern Methods", *Monographs on Oceanographic Methodology*, UNESCO,(1997), 518-519; 526-527.

Johnsen, G., et al., "Fluorescence Excitation Spectra and Light Utilization in Two Red Tide Dinoflagellates", *Limnology and Oceanography*, 42(5, Part 2), (1997), 1166-1177.

Junghans, A., et al., "Macular Pigments Lutein and Zeaxanthin as Blue Light Filters Studied in Liposomes", *Archives of Biochemistry and Biophysics*, 391(2), (2001), 160-164.

Kennedy, T. A., et al., "Peroxyl Radical Oxidation of β-Carotene: Formation of β-Carotene Epoxides", *Chem. Res. Toxicol.*, 4, (1991), 290-295.

Kimbrough, D. R., "The Photochemistry of Sunscreens", *The Journal of Chemical Education*, 74(1), (1997), 51-53.

Krinsky, N. I., "Antioxidant Functions of Carotenoids", *Free Radical Biology & Medicine*, 7, (1989), 617-635.

Liaan-Jensen, S., "Marine Carotenoids: Recent Progress", *Pure and Applied Chemistry*, 63(1), (1991), 1-12.

Llewellyn, C. A., et al., "A UV Absorbing Compound in HPLC Pigment Chromatograms Obtained From Icelandic Basin Phytoplankton", *Marine Ecology Series*, 158, (1997), 283-287.

Llewellyn, C. A., et al., "Pigment Biomarkers and Particulate Carbon in the Upper Water Column Compared to the Ocean Interior of the Northeast Atlantic", *Deep-Sea Research I*, 43(8), (1996), 1165-1184.

Lohr, M., et al., "Algae Displaying the Diadinoxanthin Cycle Also Possess the Violaxanthin Cycle", *Proc. Natl. Acad. Sci. USA*, 96, (1999), 8784-8789.

Maltby, C., "Kemin Announces Launch of New FloraGLO® Lutein Antioxidant Product for Cosmetic Applications", *Press Release, Kemin Foods*, (Oct. 21, 2003), 2 pgs.

Maoka, T., et al., "Isolation and Characterization of Dinochrome A and B, Anti-Carcinogenic Active Carotenoids from the Fresh Water Red Tide *Peridinium bipes*", *Chem. Pharm. Bull.*, 50(12), (2002),1630-1633.

Matsumura, Y., et al., "Toxic Effects of Ultraviolet Radiation on the Skin", *Toxicology and Applied Pharmacology*, 195,(2004), 298-308.

Mayer, H., et al., *In: Carotenoids*, Isler, O., Editor, Birkhauser Verlag, Basel,(1971), 325-327.

Mendes, R. L., et al., "Supercritical Carbon Dioxide Extraction of Compounds With Pharmaceutical Importance From Microalgae", *Inorganica Chimica Acta*, 356, (2003), 328-334.

Murphy, G. M., "An Update on Photoprotection", *Photodermatology, Photoimmunology and Photomedicine*, 18(1), (2002),1-4.

Olson, J. A., et al., "Introduction: The Colorful, Fascinating World of the Carotenoids: Important Physiologic Modulators", *FASEB Journal*, 9(15), (1995), 1547-1550.

Pfander, H., et al., "Carotenoid Synthesis: A Progress Report", *Pure & Applied Chemistry*, 69(10), (1997), 2047-2060.

Pinckney, J. L., et al., "Lake-Ice Algal Phototroph Community Composition and Growth Rates, Lake Bonney, Dry Valley Lakes, Antarctica", *Antarctic Journal of the United States Review 1996*, [on-line]. [retrieved Dec. 20, 2007]. Retrieved from the Internet: <URL: http://www.nsf.gov/od/opp/antarct/ajus/nsf9828/9828html/i4.htm>, (1996), 2 pgs.

Schiedt, K., et al., "Chapter 5—Isolation and Analysis", *In: Carotenoids*, vol. 1A: *Isolation and Analysis*, Britton, G., et al., Editors, Birkhauser Verlag, Basel,(1995), 81-108.

Sinha, R. P., et al., "Ultraviolet-Absorbing/Screening Substances in Cyanobacteria, Phytoplankton and Macroalgae", *Journal of Photochemistry and Photobiology B: Biology*, 47(2-3), (1998), 83-94.

Springsteen, A., et al., "In vitro Measurement of Sun Protection Factor of Sunscreens by Diffuse Transmittance", *Analytica Chimica Acta*, 380, (1999), 155-164.

Stahl, W., et al., "Antioxidant Activity of Carotenoids", *Molecular Aspects of Medicine*, 24(6), (2003), 345-351.

Valderrama, J. O., et al., "Extraction of Astaxantine and Phycocyanine from Microalgae with Supercritical Carbon Dioxide", *Journal of Chemical and Engineering Data*, 48, (2003), 827-830.

Walling, A. D., "Sunscreen and Beta-Carotene for Preventing Skin Cancer", *American Family Physician*, 61(3), (2000), [on-line]. [retrieved Mar. 12, 2007]. Retrieved from the Internet: <URL: http://www.aafp.org/afp/2000021/tips/6/html>, (2000), 2 pgs.

Young, A. J., et al., "The Xanthophyll Cycle and Carotenoid-Mediated Dissipation of Excess Excitation Energy in Photosynthesis", *Pure and Applied Chemistry*, 69(10), (1997), 2125-2130.

Zapata, M., et al., "Separation of Chlorophylls and Carotenoids From Marine Phytoplankton: A New HPLC Method Using a Reversed Phase $C_8$ Column and Pyridine-Containing Mobile Phases", *Marine Ecology Progress Series*, 195, (2000), 29-45.

Cooper, D. A., et al., "Dietary Carotenoids and Certain Cancers, Heart Disease, and Age-Related Macular Degeneration: A Review of Recent Research", *Nutrition Reviews*, 57(7), (1999), 201-214.

Dreher, F., et al., "Protective Effects of Topical Antioxidants in Humans", *In: Oxidants and Antioxidants in Cutaneous Biology. Current Problems in Dermatology*, vol. 29, (2001), 157-164.

Niles, R. M., "The Use of Retinoids in the Prevention and Treatment of Skin Cancer", *Expert Opin Pharmacother.*, 3(3), (2002), 299-303.

Tornaletti, S., et al., "UV Damage and Repair Mechanisms in Mammalian Cells", *BioEssays*, 18(3), (1996), 221-228.

Truscott, T. G., "New Trends in Photobiology—The Photophysics and Photochemistry of the Carotenoids", *Journal of Photochemistry and Photobiology, B: Biology*, (1990), 359-371.

Young, A. J., et al., "Antioxidant and Prooxidant Properties of Carotenoids", *Archives of Biochemistry and Biophysis*, 385(1), (2001), 20-27.

"European Application Serial No. 06701045.4, Amended Claim Set filed Dec. 21, 2006", 29 pgs.

"European Application Serial No. 06701045.4, Communication pursuant to Article 94(3) EPC dated Oct. 29, 2010", 5 pgs.

"European Application Serial No. 06701045.4, Communication dated Nov. 14, 2007", 4 pgs.

"European Application Serial No. 06701045.4, Communication pursiant to Article 94(3) mailed Nov. 26, 2010", 3 pgs.

"European Application Serial No. 06701045.4, Replacement Claim Set filed Aug. 21, 2007", 24 pgs.

"European Application Serial No. 06701045.4, Response filed Nov. 12, 2008 to Communication dated Nov. 14, 2007", 24 pgs.

"International Application Serial No. PCT/GB2006/000220, International Preliminary Report on Patentability mailed May 25, 2007", 15 pgs.

(56) References Cited

OTHER PUBLICATIONS

"Machine Translation of JP 07-101872A", 5 pgs., Apr. 18, 1995.
Arsalane, W., et al., "Influence of the Pool Size of the Xanthophyll Cycle on the Effects of Light Stress in a Diatom: Competition Between Photoprotection and Photoinhibition", *Photochemistry and Photobiology*, 60(3), (1994), 237-243.

Hager, A., "The reversible, light-induced conversions of xanthophylls in the chloroplast", *In: Pigments in Plants*, Czygan, F. C., Editor, (Fischer, Stuttgart, Germany), (1980), 57-79.
Kiebassa, C., et al., "Wavelength dependence of oxidative DNA damage induced by UV and visible light", *Carcinogenesis*, 18(4), (1997), 811-816.

* cited by examiner (I)

(II)

(III)

SUNSCREEN COMPOSITIONS COMPRISING CAROTENOIDS

RELATED APPLICATIONS

This application is a nationalization under 35 U.S.C. 371 of PCT/GB2006/000220, filed Jan. 23, 2006 and published as WO 2006/077433 A1 on Jul. 27, 2006, which claimed priority under 35 U.S.C. 119 to United Kingdom Patent Application Serial No. 0501365.1, filed Jan. 21, 2005; which applications and publication are incorporated herein by reference and made a part hereof.

The present invention relates to compositions comprising algae-derived compounds diadinoxanthin, diatoxanthin, fucoxanthin and related compounds. Preferably the compositions are pharmaceutical or cosmetic compositions, particularly compositions with photoprotective properties, such as sunscreens for preventing damage resulting from exposure of body coverings or surfaces such as skin and hair to the UV- and visible range of the solar spectrum.

Sunlight is composed of a continuous spectrum of electromagnetic radiation that is divided into three main regions of wavelengths: ultraviolet (UV), visible, and infrared. UV radiation comprises the wavelengths from 200 to 400 nm, while visible light ranges from 400 to 700 nm. The ultraviolet spectrum is further divided into three sections, each of which has distinct biological effects: UVA (320-400 nm), UVB (280-320 nm), and UVC (200-280 nm).

The damaging effects of sunlight on skin are well documented, and the multiple deleterious effects include burns, premature aging and wrinkling of the skin (dermatoheliosis), development of pre-malignant lesions (solar keratoses) and various malignant tumours.

While the UVC rays are effectively blocked from reaching the Earth's surface by the stratospheric ozone layer, UVA and UVB radiation both reach the Earth's surface in amounts sufficient to have important biological consequences to the skin and eyes. Of the UV radiation that reaches the surface of the earth, 90-99% is comprised of UVA and 1-10% is comprised of UVB. The damaging effects of UVB have been widely documented. The short term effects of these high intensity rays include erythema and burns. In the longer term the risk of skin cancer is significant as UV radiation from 245 to 290 nm is absorbed maximally by DNA, and is able to directly induce mutagenic photoproducts or lesions in DNA among adjacent pyrimidines in the form of dimers.

UVA rays are not directly absorbed by DNA, but can have indirect harmful effects by forming radical oxygen species that can react with cellular proteins and DNA. The UVA rays are lower in intensity; they penetrate below the skin surface and cause long-term damage such as premature wrinkling and photoaging, and are believed to be carcinogenic. Skin cancer is the most common type of cancer, in the US about 800 000 cases occur each year. Most skin cancers are either basal cell or squamous type and tend to grow and spread slowly. Malignant melanoma is a much more serious form of skin cancer and is now increasing by about 4% per year.

The exact wavelength of radiation in the solar spectrum which induces melanoma is not known, but the limited data that are available suggest that the UVR spectrum is most important, particularly UVB but possibly also UVA and visible blue light. With the growing awareness that UVA damage exacerbates the risk of melanoma and other tumours, the need for broad spectrum protection has become obvious. The classical means of measuring sunscreen efficiency is the sun protection factor (SPF) number, which is defined as the prolonged exposure to UVB rays the skin can endure before getting burned, compared to untreated skin. Several studies speak of the potentially dangerous false sense of security the SPF factor gives with regards to damage induced by UVA and visible blue light.

In view of their convenience of use, sunscreens have assumed a major component of protection against sun rays. Sunscreens work by absorbing, reflecting or scattering the sunrays, and thereby either shielding the skin from the sun's rays or transforming the light energy to a harmless energy form. Sun protecting agents can roughly be divided into chemical and physical filters. The physical sunscreens are inorganic microparticles that act as broad spectrum photoprotectors by reflecting or scattering the sunrays. Extensively used physical barriers include zinc oxide and titanium dioxide. They are known to provide good photoprotection but are less appealing cosmetically; they are not absorbed by the skin and tend to stay as a white layer on the skin surface.

Chemical sunscreens are absorbed by the skin, and exert their sunscreen activity by absorbing the rays emitted by the sun and re-emitting this light energy as vibrational energy (heat). Common chemical sunscreen agents include PABA (para-amino benzoic acid) and its derivatives, cinnamates, salicylates, anthranilates, camphor derivatives, benzimidazole, triazones, octocrylene, urocanic acid, bisimidazylate and anisotriazine.

Consumer safety is a major concern with regards to sunscreen compounds. Available research establishes that some sunscreen compounds are potentially photo allergic; for example PABAs, that are known to induce photo allergic reactions in 1-2% of the population (Kimbrough, 1997, J. Chem. Ed., 74(1), p51-53). Although generally regarded as good photo protectors, the safety of the physical sunscreen has also been discussed, as in vitro studies with human fibroblasts has shown formation of hydroxyl radicals upon the combination of sun exposure and titanium dioxide, which led to strand breakage in the DNA (Dunforda et al, 1997, FEBS Lett., 418, p87-90). In addition, all of these chemicals photo decompose into unknown compounds and the long-range safety effects have not been studied.

There is particularly a need for a good means for rating UVA protection, as no such standard exist today. Despite increasing awareness of the importance of broad spectrum protection, studies show that commercially available sunscreens claiming to have good UVA protection do not protect sufficiently against UVA rays (Haywood et al, 2003, J. Invest. Derm., 121(4), p862). Particularly, in the longer wavelength UVA radiation (370-400 nm) the available sun filters provide poor protection and particularly poor or no protection against wavelengths above 400 nm.

Most of the commercially available UV- and sun protecting compounds in skin creams are synthetic, and the search for natural compounds with equal or greater efficiency is becoming more significant because of the consumer's preference for natural products.

The UV-absorbing properties of various organisms and natural extracts have been studied among higher plants, corals, cyanobacteria and phytoplankton, but commercialization of natural sunscreen compounds is still limited. There remains a need for naturally derived sun-absorbing or sunscreen agents that are efficient filters of sun in the UV- and visible range of the solar spectrum.

Surprisingly a discrete family of carotenoids in the xanthophyll group have been identified which are effective UV and visible light filters (particularly for use on the skin of animals, especially humans), are antioxidants, have a golden yellow colour, are oil soluble and stable. This family are embodied by the carotenoids diadinoxanthin, diatoxanthin, fucoxanthin and their derivatives.

Diadinoxanthin, diatoxanthin and fucoxanthin are carotenoids in the xanthophyll group, found in 50' of the 10 world wide important bloom-forming phytoplankton classes: Diatoms, Dinoflagellates, Prymnesiophytes, Euglenophytes, Chrysophytes. Fucoxanthin is also present in abundance in other organisms, e.g. seaweed, raphidocytes and brown algae (macroalgae) such as *Fucus vesiculosus*.

Diatoms, dinoflagellates and Prymnesiophytes are characterized by having the ability to synthesize significant amounts of diadinoxanthin and diatoxanthin under high-light conditions in spring and summertime, while staying in shallow brackish top layers in fjords, coastal areas and along the ice edge.

These organisms have developed efficient photoprotective mechanisms in order to minimize photoinhibition that could result from their periodic exposure to excess light intensities. Among the short-term defenses that are activated by a sudden increase in light intensity, the photoprotective radiative dissipation of excess absorbed light energy is known as an important mechanism. In this mechanism the xanthophylls diadinoxanthin and diatoxanthin are involved, in a process referred to as non-photochemical quenching (NPQ). Diadinoxanthin is localized in a major light harvesting pigment-protein complex (LHC), where it normally receives light energy and sends it to reaction centres in photosystem II (PS II). In NPQ diadinoxanthin is de-epoxydized to diatoxanthin, which has an active role in dissipating excess light energy instead of sending it to the reaction centre.

The present inventors have found that diadinoxanthin, diatoxanthin, fucoxanthin and related compounds have particularly useful properties as sunscreens, particularly when applied to living organisms.

The compounds have not previously been identified as having any utility as sun-absorbing compounds. Diadinoxanthin and diatoxanthin in particular are rare carotenoids, and were considered difficult to isolate and of poor stability. Particularly when diadinoxanthin and fucoxanthin occur together in a biological system, a method of isolating both compounds simultaneously has been assumed to be particularly difficult. The inventors have now isolated the compounds in stable form and investigated their properties. These carotenoids have surprisingly been found to be useful in absorbing irradiation, particularly in the previously overlooked blue light range and thus have utility in applications reliant on sun-absorbing properties, e.g. as sunscreens.

In a first aspect, the present invention provides a composition comprising a carotenoid, preferably a xanthophyll, a hydroxy carotenoid (particularly a di-hydroxy-carotenoid) or epoxy carotenoid, wherein said carotenoid contains an optionally substituted, linear unsaturated alkyl chain comprising conjugated double bonds, substituted at each end of the chain by a cyclic alkyl group and wherein said alkyl chain contains at least one $-C_3R_1R_2-$ group, wherein $R_1$ and $R_2$ may be the same or different and are each a hydrogen atom, a hydroxy group or an alkyl group or together with the carbon atom to which it is attached may form part or all of one of said cyclic alkyl groups or a pharmaceutically acceptable derivative or salt thereof.

Preferably said $-C_3R_1R_2-$ group is selected from one of the following groups:

$-CR_1=C=CR_2-$, $-C\equiv C-CR_1R_2-$ and $-CR_1R_2-C\equiv C-$ wherein preferably $R_1$ or $R_2$ is hydrogen and the other R group (or both $R_1$ and $R_2$) together with the carbon atom to which it is attached is part or all of a terminal cyclic alkyl group.

Alternatively described the carotenoid comprises  or $-CR_3 \cdots C \equiv CR_2-$ wherein only one of the optional bonds is present, and $R_1$ or $R_2$ may be absent or present together on a terminal carbon atom depending on the bonds which are present.

In a particularly preferred feature, the carotenoid has the formula:

$$R_3-[C_3R_1R_2]_a-[CR_4]_b-[C_3R_1R_2]_c-R_5$$

wherein
a and c are each an integer from 0 to 2 wherein a+c is $\geq 1$, preferably=1;
b is an integer from 6 to 25, especially preferably 11, 13, 14, 16, 17 or 19;
$R_1$ and $R_2$ are as defined hereinbefore;
$R_3$ and $R_5$, may be the same or different and are each a cyclic alkyl group or a portion of a cyclic alkyl group and the remainder of said cyclic group is provided by $R_1$, $R_2$ or $R_4$ (or $R_1$ and $R_2$), together with the carbon atom to which it is attached; and
$R_4$ is an optionally substituted alkyl group, a hydrogen atom, an oxygen atom or hydroxy group or together with the carbon atom to which it is attached may form part or all of one of said cyclic alkyl groups, wherein if $R_4$ is an oxygen atom and thereby provides a carbonyl group, the adjacent carbon atom carries two $R_4$ groups, preferably hydrogen atoms.

Such compounds may therefore take the formula:

wherein relative to the preceding formula, $R_4$ is represented by $R_{4a}$ to $R_{4s}$, (wherein optionally $=CR_{4r}-CR_{4s}=$ may be absent), a is 0, b is 17 or 19, c is 1, $R_3$ together with $R_{4a}$ and the carbon atom to which they are attached forms a cyclic group, and $R_5$ together with $R_2$ and the carbon atom to which they are attached forms a cyclic group. (In an alternative embodiment, the group $-CR_1CCR_2R_5$ in the formula above, may be replaced with the group $-C\equiv C-CR_1R_2R_5$.)

Optionally a $-CR_4CR_4-$ group may be replaced with a $-CR_4R_4CO-$ group as described hereinbefore. In a preferred feature said $-CR_4CR_4-$ group is $-CR_{4b}CR_{4c}-$. One or more of $R_{4a}$ to $R_{4s}$ is preferably an alkyl group, especially preferably $R_{4d}$, $R_{4h}$, $R_{4m}$ and $R_{4q}$ are alkyl groups, preferably methyl groups.

Preferred cyclic groups (which may be the same or different at either end of the hydrocarbon chain) are optionally substituted aromatic or non-aromatic hydrocarbons, prefer- ably hexyl groups. The cyclic group is preferably a substituted cyclohexyl, cyclohexenyl group (e.g. 1-cyclopenten-1-yl) or the cyclohexane bivalent radical cyclohexylidene, wherein such groups are preferably substituted at one or more of the ring carbons by an alkyl group, epoxy group, hydroxy group or carbonyl group, which themselves may be further substituted.

In a particularly preferred feature, the cyclic group is a cyclohexyl group and C2 of the hexyl group is substituted with a hydroxy group or an alkyl group (preferably a methyl group) (and/or C1 and C2 carry an epoxide group), C4 is substituted with an alkyl group (preferably a methyl group), and/or a hydroxy group (which itself may be substituted by a carbonyl group, e.g. to give an acetoxy group) and C6 is bi-substituted with alkyl groups, preferably methyl groups.

As referred to herein alkyl groups may be mono- or poly-unsaturated and include both alkenyl and alkynyl groups. Such groups may contain up to 40 carbon atoms.

The alkyl chain is preferably C15-C25, e.g. C19-C23. Substituent alkyl groups are preferably shorter, e.g. preferably alkyl groups contain up to 10, e.g. from 1 to 5 carbon atoms. In particular straight-chained saturated hydrocarbons, e.g. with 1, 2 or 3 carbon atoms are preferred. Substituted alkyl groups may be mono or poly-substituted, e.g. they may be alkoxyalkyl, hydroxyalkoxyalkyl, polyhydroxyalkyl, hydroxy poly alkyleneoxyalkyl, oxyalkyl, polyoxaalkyl and the like.

Cyclic groups may thus be selected from the group comprising:

γ

β

ε

χ

κ

φ which reflect commonly found cyclic groups in carotenoids, wherein the indicated R group corresponds to the rest of the molecule and C16, C17 and/or C18 may be replaced with an alkyl or oxygen-containing group as described above and where appropriate the cyclohexenyl ring converted into a cyclohexyl ring and/or C3 may be substituted with an alkyl or oxygen-containing group as described above. Preferred cyclic groups according to the invention are:

(I)

(II)

(III)

The preferred compounds are thus carotenoids containing one or more alkadienylene or alkynylene groups (preferably one or more propdienylene or ethynylene groups) in the hydrocarbon chain, wherein the alkadienylene or alkynylene group may include a carbon which is part of a terminal cyclic group.

Carotenoids of the invention are based on the carotene structure with optionally substituted β, ε, γ, κ, φ or λ cyclic groups, as described hereinbefore. Such carotenoids have at least one didehydro group, preferably at one or more of the positions corresponding to the position selected from: a) 6,7; b) 6',7'; c) 7,8; and d) 7',8' on the carotene structure. Especially preferably, a didehydro group is present at positions 6',7' and/or 7',8'.

Preferably the above described family does not encompass naturally occurring carotenoids, other than specifically mentioned carotenoids described herein in accordance with the invention, e.g. fucoxanthin, diatoxanthin and diadinoxanthin and preferably also their naturally occurring derivatives such as their seco-, apo- or nor-carotenoid derivatives or degradation products. In a preferred feature the above described family does not extend to alloxanthin, neoxanthin, crocoxanthin or vaucheriaxanthin, especially preferably neoxanthin.

Especially preferably the carotenoid is: 5,6-epoxy-3,3',5'-trihydroxy-6',7'-didehydro-5,6,7,8,5',6'-hexahydro-β,β-caroten-8-one 3'-acetate (preferably 3S,5R,6S,3'S,5'R,6'R);

5,6-epoxy-7',8'-didehydro-5,6,dihydro-β,β-carotene-3,3'-diol (preferably 3S,5R,6S) or 7',8'-didehydro-β,β-caroten-3,3'-diol (preferably 3R,3'R).

Figure 1:
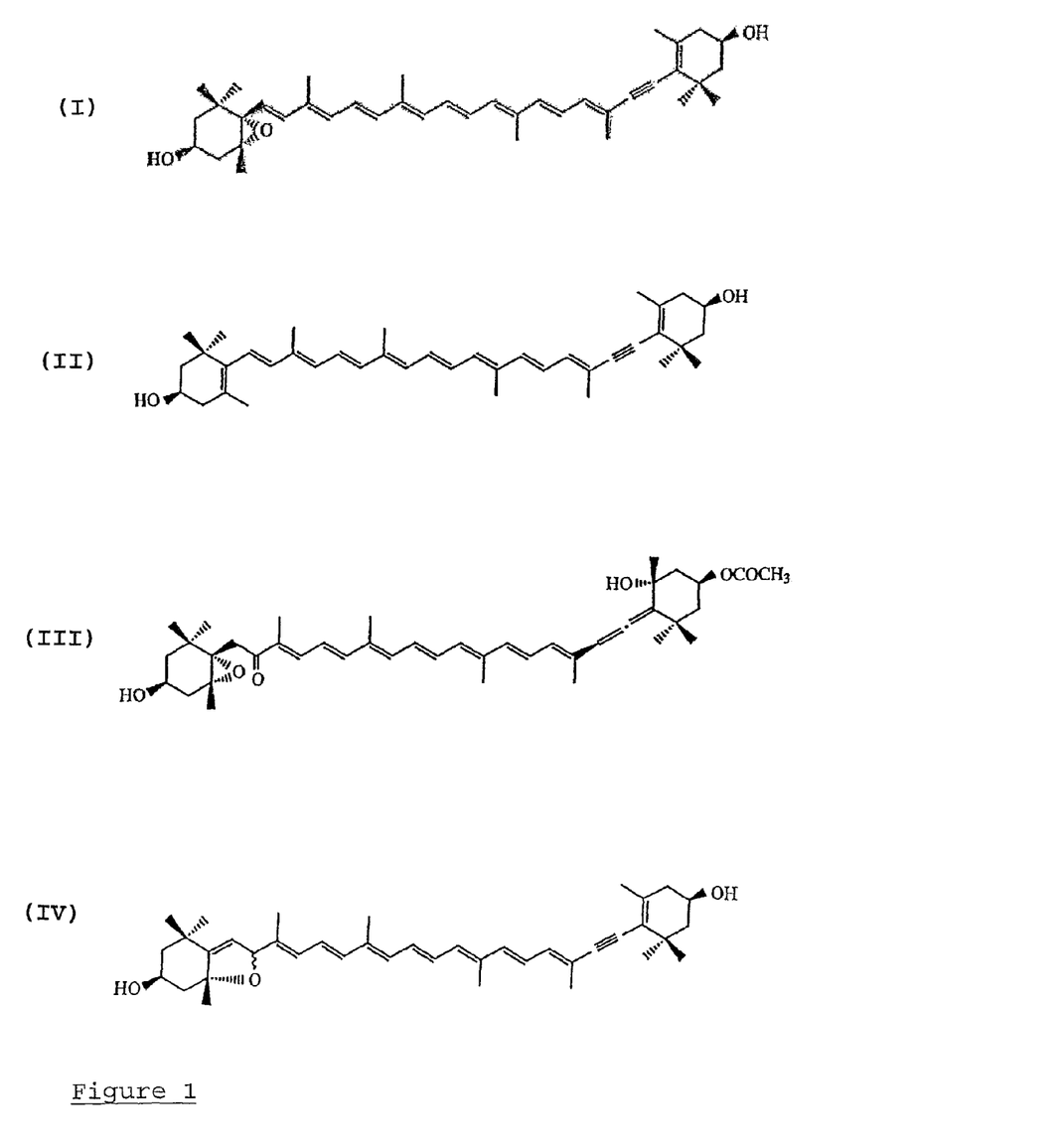
FIG. 1 shows the chemical structure of diadinoxanthin (I), diatoxanthin (II), fucoxanthin (III) and diadinochrome (IV)
Figure 2:
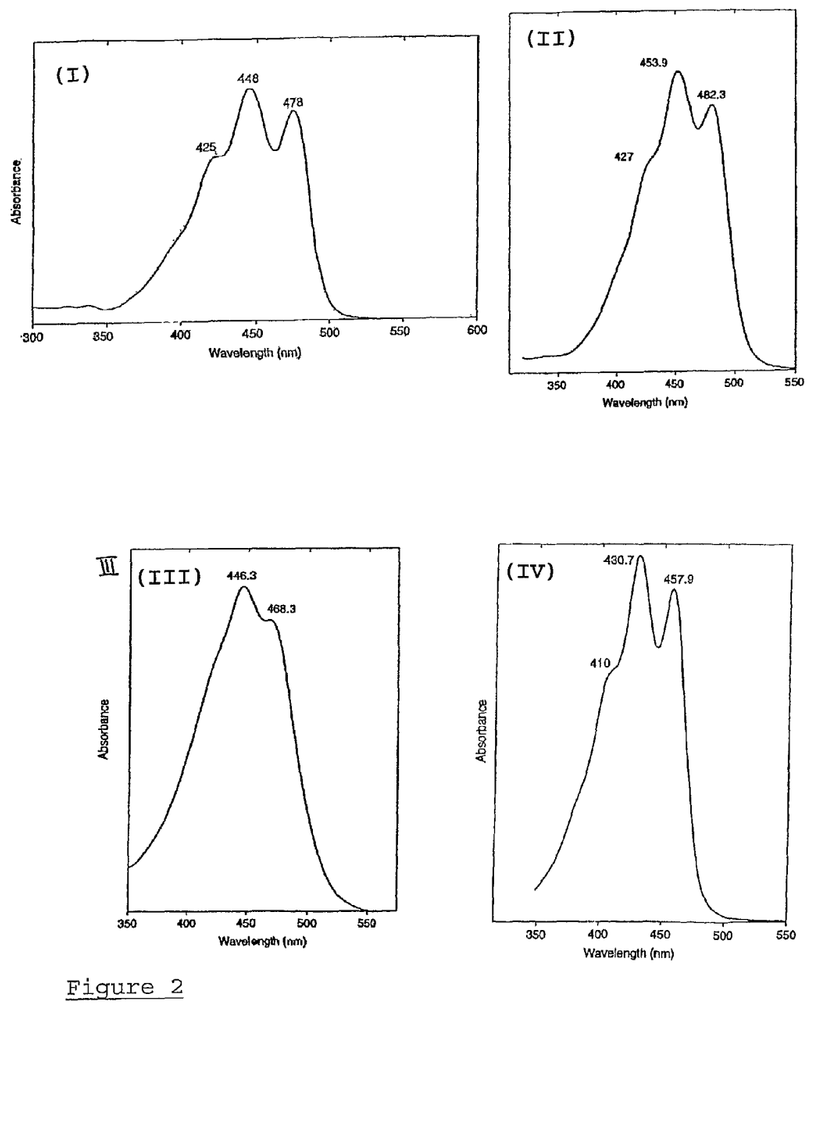
FIG. 2 shows the absorption spectrum of diadinoxanthin (I), diatoxanthin (II), fucoxanthin (III) and diadinochrome (IV) in acetone solution.

Especially preferably said compound is diadinoxanthin, diatoxanthin or fucoxanthin which have the structures shown in FIG. 1.

In a particularly preferred aspect, the carotenoid has the formula:

$$R_3-CR_{4a}-CR_{4b}-CR_{4c}-CR_{4d}-CR_{4e}-CR_{4f}-$$
$$CR_{4g}-CR_{4h}-CR_{4i}-CR_{4j}-CR_{4k}-CR_{4l}-$$
$$CR_{4m}-CR_{4n}-CR_{4o}-CR_{4p}-C_3-R_1R_2-R_5$$

wherein
$R_1$ is a hydrogen atom when $-C_3R_1R_2-$ is $-CR_1=C=CR_2-$ or forms part of a cyclic group together with $R_2$ and $R_5$, when $-C_3R_1R_2-$ is $-C\equiv C-CR_1R_2-$;
$R_3$ is a cyclic group selected from cyclic groups I, II and III (as defined hereinbefore);
each of $R_{4a}$ to $R_{4p}$ is an optionally substituted alkyl group, a hydrogen atom, an oxygen atom or a hydroxy group, wherein if $R_4$ is an oxygen atom the adjacent carbon atom carries two $R_4$ groups, preferably $R_{4a}$, $R_{4b}$, $R_{4d}$, $R_{4e}$, $R_{4f}$, $R_{4h}$, $R_{4i}$, $R_{4j}$, $R_{4k}$, $R_{4m}$, $R_{4n}$, $R_{4o}$ are hydrogen atoms and $R_{4c}$, $R_{4g}$, $R_{4l}$, $R_{4p}$ are methyl groups or $-CR_{4a}-CR_{4b}-$ is the group $-CH_2-CO-$;
$R_5$ is a portion of a cyclic group which cyclic group may be the same as or different to $R_3$ and the remainder of said cyclic group is provided by $R_2$ and the carbon to which it is attached when $-C_3R_1R_2-$ is $-CR_1=C=CR_2-$ or is provided by $R_1$ and $R_2$ together with the carbon atom to which they are attached when $-C_3R_1R_2-$ is $-C\equiv C-CR_1R_2-$, or a pharmaceutically acceptable derivative or salt thereof.

Especially preferably $R_3$ is cyclic group I or III and $R_5$ (together with $R_2$ or $R_1$ and $R_2$) is cyclic group I or II, preferably I and preferably $-C_3R_1R_2-$ is $-C\equiv C-CR_1R_2-$.

In an especially preferred aspect, the carotenoid has the formula:

$$R_3-CR_{4a}-CR_{4b}-CR_{4c}-CR_{4d}-CR_{4e}-CR_{4f}-$$
$$CR_{4g}-CR_{4h}-CR_{4i}-CR_{4j}-CR_{4k}-CR_{4l}-$$
$$CR_{4m}-CR_{4n}-CR_{4o}-CR_{4p}-C\equiv C-R_6$$

wherein
$R_3$ and $R_6$, which may be the same or different, are each a cyclic group selected from cyclic groups I and III (as defined hereinbefore);
each of $R_{4a}$ to $R_{4p}$ is an optionally substituted alkyl group, a hydrogen atom, an oxygen atom or a hydroxy group, wherein if $R_4$ is an oxygen atom the adjacent carbon atom carries two $R_4$ groups, preferably $R_{4a}$, $R_{4b}$, $R_{4d}$, $R_{4e}$, $R_{4f}$, $R_{4h}$, $R_{4i}$, $R_{4j}$, $R_{4k}$, $R_{4m}$, $R_{4n}$, $R_{4o}$ are hydrogen atoms and $R_{4c}$, $R_{4g}$, $R_{4l}$, $R_{4p}$ are methyl groups, or a pharmaceutically acceptable derivative or salt thereof.

Preferably $R_6$ is cyclic group I. (When $R_3$ and $R_6$ is cyclic group I the compound is diatoxanthin and when $R_3$ is cyclic group III and $R_6$ is cyclic group I the compound is diadinoxanthin.)

Pharmaceutically acceptable derivatives, which are described in more detail hereinafter, include degradation products such as diadinochrome in which relative to the formula above $R_3-CR_{4a}-CR_{4b}-$ is a fused heterocyclic group in which the oxygen of the epoxide group of cyclic group III forms a bond with the alkyl chain comprising conjugated double bonds to form a 5-membered heterocyclic group comprising an oxygen atom, $CR_{4a}-CR_{4b}$ from the alkyl chain and 2 carbon atoms from cyclic group III.

In an alternative preferred aspect, the carotenoid has the formula:

$$R_3-CR_{4a}-CR_{4b}-CR_{4c}-CR_{4d}-CR_{4e}-CR_{4f}-$$
$$CR_{4g}-CR_{4h}-CR_{4i}-CR_{4j}-CR_{4k}-CR_{4l}-$$
$$CR_{4m}-CR_{4n}-CR_{4o}-CR_{4p}-CH=C=R_7;$$

wherein
$R_3$ and $R_7$, which may be the same or different, are each a cyclic group selected from cyclic groups II and III (as defined hereinbefore);
$-CR_{4a}-CR_{4b}-$ is the group $-CH_2-CO-$;
each of $R_{4c}$ to $R_{4p}$ is an optionally substituted alkyl group, a hydrogen atom, an oxygen atom or a hydroxy group, wherein if $R_4$ is an oxygen atom the adjacent carbon atom carries two $R_4$ groups, preferably $R_{4d}$, $R_{4e}$, $R_{4f}$, $R_{4h}$, $R_{4i}$, $R_{4j}$, $R_{4k}$, $R_{4m}$, $R_{4n}$, $R_{4o}$ are hydrogen atoms and $R_{4c}$, $R_{4g}$, $R_{4l}$, $R_{4p}$ are methyl groups, or a pharmaceutically acceptable derivative or salt thereof.

Preferably $R_3$ is cyclic group III and preferably $R_7$ is cyclic group II.

By "pharmaceutically acceptable" or "physiologically acceptable" is meant that the ingredient must be compatible with other ingredients in the composition as well as physiologically acceptable to the recipient.

Pharmaceutically acceptable derivatives (which have the same or similar functional properties to the compounds described above), include isomers ranging from all trans to a mixture of cis-trans to all cis isomers and includes optical isomers (e.g. 3S, 5S, 6R, 3'R and 3S, 5R, 6S, 3'R for diadinoxanthin). Derivatives further include molecules which have been modified by e.g. modification of the hydrocarbon backbone, e.g. by substitution with one or more alkyl groups or modification of either or both of the cyclic groups (e.g. as described hereinbefore), providing such modifications do not alter the functional properties of the compounds as described herein. For example, derivatives extend to esters, e.g. the carotenoids may be esterified with fatty acids.

Derivatives also extend to derivatives, which may occur naturally, such as seco-, apo- and nor-carotenoid derivatives. Seco-carotenoids refers to carotenoid derivatives which have undergone oxidative fission without the loss of any carbon atoms. Apo-carotenoids are derivatives in which the carbon skeleton is shortened during oxidative fission and nor-carotenoids are derivatives in which carbon atoms have been removed by processes other than cleavage of carbon-carbon bonds. Derivatives thus extend to truncated carotenoids, e.g. in which one or more isoprene units are removed from the isoprene polymer chain.

Derivatives also include epoxide derivatives and their 5,8 epoxide isomers. Degradation products, e.g. in which the carbonyl group of fucoxanthin is reacted e.g. with sodium borohydride in ethanol are also included. As mentioned above, the compound product diadinochrome is a representative degradation product of diadinoxanthin. Dehydration derivatives, e.g. generated after treatment of the compounds described hereinbefore with hydrogen chloride in chloroform, are also included.

Derivatives may also be generated to modify compounds of the invention for their use in cosmetic and pharmaceutical applications, e.g. by the addition of targeting or functional groups, e.g. to improve lipophilicity, aid cellular transport, solubility and/or stability. Thus oligosaccharides, fatty acids, fatty alcohols, amino acids, peptides or proteins may be conjugated to the aforementioned compounds. Derivatives may be in the form of "pro-drugs" such that the added component may be removed by cleavage once administered, e.g. by cleavage of a substituent added through esterification which may be removed by the action of esterases.

Derivatives which retain functional activity may be tested to establish if they retain the desired properties by the test described herein e.g. to determine photoprotective properties.

The active ingredient for administration may be appropriately modified for use in a pharmaceutical composition. For example the compounds used in accordance with the invention may be stabilized against degradation by the use of derivatives as described above.

The active ingredient may also be stabilized in the compositions for example by the use of appropriate additives such as salts or non-electrolytes, acetate, SDS, EDTA, citrate or acetate buffers, mannitol, glycine, HSA or polysorbate.

Pharmaceutically acceptable salts are preferably acid addition salts with physiologically acceptable organic or inorganic acids. Suitable acids include, for example, hydrochloric, hydrobromic, sulphuric, phosphoric, acetic, lactic, citric, tartaric, succinic, maleic, fumaric and ascorbic acids. Hydrophobic salts may also conveniently be produced by for example precipitation. Appropriate salts include for example acetate, bromide, chloride, citrate, hydrochloride, maleate, mesylate, nitrate, phosphate, sulfate, tartrate, oleate, stearate, tosylate, calcium, meglumine, potassium and sodium salts. Procedures for salt formation are conventional in the art.

Preferably the compounds used in compositions and uses of the invention are obtained or derived from naturally occurring sources. They may however be generated entirely or partially synthetically (e.g. from commercially available carotenoids such as β-carotene, astaxanthin, lutein or zeaxanthin), or derivatized after purification. Preferably the compounds are isolated from natural sources, preferably macro or microalgae, particularly microalgae belonging to the phytoplankton classes Diatoms, Dinoflagellates, Prymnesiophytes, Euglenophytes, Chrysophytes, especially preferably from the diatoms *Phaeodactulym tricornutum* or *Procentrum minimum* or the microalgae *Prymnesium parvum*.

Fucoxanthin may additionally be isolated from various other sources, such as any seaweed (Kingdom: Protists, Divison: Phaeophyta) e.g. including *Fucus vesiculosus* as mentioned hereinbefore, *Fucos serratus* and *Laminaria Hyperborea*. Other sources include: *Undaria pinnitifida, Sargassum muticum, Macrocystis pyrifera, Macrocystis angustifolia, Padina boryana, Ecklonia maxima, Laminaria pallida, Ecklonia biruncinata, Pelagophycus porra, Turbinaria ornata, Bifurcaria brassicaeformis* and *Splachnidium rugosum*.

Compounds of the invention may be isolated from natural sources or isolated from natural sources which have been modified to allow production of the carotenoids used in the invention, e.g. by transformation of microbiological organisms to produce the required synthetic enzymes and isolation of the compounds from those organisms.

Conveniently such compounds are isolated by techniques known in the art such as by partition and chromatography (see Haugan & Liaaen-Jensen, 1989, Phytochemistry, 28(10), p2797-2798) or HPLC (Zapata et al., 2000, MEPS, 195, p29-45). The Britten method may also be used for isolation, e.g. of fucoxanthin (Britton et al. and Schiedt & Liaaen-Jensen, 1995, in "Carotenoids, Volume 1A: Isolation and Analysis", Eds. Britton et al., Birkhauser Verlag, Base1, p13-16 and p81-108, respectively). The compounds may also be isolated by supercritical $CO_2$ extraction which has been used for carotenoid isolation (Mendes et al., 2003, Inorganica Chimica Acta, Vol. 356, p328-334; Valderrama et al., 2003, J. Chem. Eng. Data, 48, p827-830).

Compounds for use in compositions of the invention may also be isolated in accordance with the protocols described in the Examples. Such methods and the products of such methods form further aspects of the invention. Thus in a further aspect the present invention provides a method of purifying a carotenoid from algae comprising the steps of (i) mixing algae with water adjusted to a pH of 8 to 12 (preferably pH 8-10, e.g. pH 8.3), (ii) adding alcohol, preferably ethanol (or alternatively methanol), to a final water:alcohol ratio of 0.2 to 1.5:1.0 (preferably 0.3 to 1.0:1, e.g. 0.3:1), (iii) extracting said alcohol-water mixture (aqueous phase) with a liquid organic solvent (organic phase), preferably heptane (or alternatively hexane), at a water-alcohol:organic solvent ratio of 0.75 to 1.5:1.0 (preferably 1-1.4:1, e.g. 1.3:1), (iv) optionally cooling said organic phase e.g. at less than 10° C., e.g. ≤5, 0, −5, −10 or −20° C. (e.g. 5-10° C.) for more than 5 minutes, e.g. 15-60 minutes, or for longer, e.g. for 12-26 hours, e.g. 24 hours; and (v) collecting the aqueous and/or organic phase and purifying the carotenoid therefrom.

In the above described method, the order in which the water, alcohol and organic solvent is added is not crucial. Thus the alcohol and water may be added to one another and then the organic solvent may be added, or the alcohol and organic solvent may be mixed, followed by the addition of the water.

Preferably said method is used for isolation of diadinoxanthin, diatoxanthin and/or fucoxanthin wherein diadinoxanthin and diatoxanthin is isolated from the organic phase and fucoxanthin is isolated from the aqueous phase. Step (iii) is preferably performed by mixing for 30-90 minutes, e.g. 1 hour at ambient temperature, e.g. 15-25° C., e.g. around 20° C. Specific variations of the general method are described in the Examples.

The alcohol for use in the method is liquid at room temperature and is soluble in water, but not heptane and is preferably ethanol or methanol, though other alcohols such as propanol may be used. Organic solvents are substantially immiscible in water and are preferably liquid at −20° C., e.g. heptane, hexane or pentane.

Compounds thus isolated are preferably substantially free of any contaminating components derived from the source material or materials used in the isolation procedure. Especially preferably the compound is purified to a degree of purity of more than 50 or 60%, e.g. >70, 80 or 90%, preferably more than 95 or 99% purity as assessed w/w (dry weight). Such purity levels correspond to the specific compound of interest, but including its isomers and optionally its degradation products. Where appropriate, enriched preparations may be used which have lower purity, e.g. contain more than 1, 2, 5 or 10% of the compound of interest, e.g. more than 20 or 30%.

Conveniently the level of purity may be assessed by analysis, e.g. using UV/visible spectrophotometry, HPLC analysis or mass spectrometry. Synthetically generated or modified compounds should be similarly free from contaminating components.

Carotenoids used in accordance with the invention may be generated synthetically based, for example, on a synthetic carbon skeleton. Such skeletons may be generated using techniques known in the art, such as Witting type reactions, Grignard and Nef reactions, enol ether condensations, Reformatsky reactions, Robinson's Mannic base synthesis, reductive or oxidative dimerizations and Wurtz reactions (see e.g. Haugan, Dr. Ing. thesis, University of Trondheim, NTH, 1994, from p155 and Mayer & Isler, 1971, in "Carotenoids", Ed. Isler, Birkhäuser, Base1, p325).

The carbon skeleton may then be modified accordingly to generate the carotenoid of interest using techniques known in the art. For example, fucoxanthin may be synthesized as described (Ito et al., 1994, Pure & Appl. Chem., 66(5), p939-946) in which a C10 carbon skeleton portion was condensed with molecules providing the cyclic end groups. The synthesis of diatoxanthin is described in Haugan et al., 1994, supra, p165-205. Diadinoxanthin may be prepared for example, from diatoxanthin by the introduction of an epoxy group at the 5'-6' or 5-6 double bond of diatoxanthin. Derivatives of these synthetically prepared carotenoids may be made as described above using techniques known in the art.

The carotenoid compound may be present in said compositions as the sole active ingredient or may be combined with other ingredients, particularly other active ingredients, e.g. to increase the range over which light protection may be offered and/or to change the physical or chemical characteristics of the product or to make it appealing to the consumer. Thus for example one or more additional sunscreen compounds may be included in the composition or co-administered with the composition. Chemical or physical sunscreen agents may be used, e.g. as described hereinbefore which are able to absorb/quench radiation, particularly solar radiation, particularly in the UVB and shorter UVA range or infrared region of the spectrum. Compounds which may be used include UVB/UVA2 filters (which filter in the range 290-340 nm) such as octyl methoxy-cinnamate, oxybenzone, octyl salicylate, homosalate, octocrylene, padimate O, menthyl anthranilate and 2-phenylbenzimadazole-5-sulfonic acid. UVA1 filters (filtering in the range 340-400 nm) include avobenzone, zinc oxide and titanium dioxide. Preferably however, compounds are used which are found naturally, e.g. other carotenoids, (e.g. as described herein), mycosporine-like amino acids or scytonemin.

Carotenoids as described herein may be used in combination. Thus for example preferred compositions in accordance with the invention may include two or more carotenoids as described herein, e.g. two or more compounds selected from diadinoxanthin, diatoxanthin, diadinochrome and fucoxanthin, especially preferably diadinoxanthin and fucoxanthin.

The composition of the invention may be used in various biological and non-biological applications. Thus the compositions may be used in any non-biological material in which photoprotective (or colouring) properties are desirable, e.g. in plastics, paints, waxes, windows (of buildings or vehicles), solar panels, windshields, stains or lacquers, glass, contact lenses, synthetic lenses to avoid photodamage or sun damage (e.g. bleaching) to the product to which they are applied, or to the biological entity to which sunprotection is to be offered. The compounds of the invention may be applied to such materials or impregnated into those materials.

The invention thus further extends to a method of preparing a photoprotective or photoprotected product comprising applying a compound or composition of the invention to said product, or impregnating said product with said compound or composition. The use of compounds or composition of the invention to prepare such products is also considered an object of the invention. Photoprotected or photoprotective products thus formed form further aspects of the invention.

Preferably the compositions of the invention are pharmaceutical compositions comprising a compound as described hereinbefore and one or more pharmaceutically acceptable excipients and/or diluents as described hereinafter.

The compounds described herein have photoprotective, colouring and antioxidant properties.

The compositions as described herein may thus be used in cosmetic or medical applications. The pharmaceutical composition described herein may therefore be a cosmetic composition, an antioxidant composition or a light protection filter or sunscreen. The present invention further provides such compositions for use as a medicament.

The compounds described herein have an attractive golden colour and therefore may be used in cosmetics which take advantage of that colouring or add an additional property to sunscreens of the invention. Thus the sunscreen and/or cosmetic preparations described herein preferably have 2 or more properties, selected from colouring, sunscreen and antioxidant properties. As an alternative or complementary to this property as a colorant the compounds may be used for their antioxidant or photoprotective properties.

Thus in a further aspect the present invention provides compositions as described herein as a cosmetic, sunscreen (light protection filter) or antioxidant.

As referred to herein, a "cosmetic" refers to a composition used on a human or non-human animal for non-medical purposes.

As used herein a "sunscreen" or "light protection filter" or "photoprotective composition" refers to a composition which is suitable for administration to an individual which provides protection against light irradiation (i.e. acts as a light or sun-absorbing compound), particularly of ultraviolet and visible light, preferably wavelength 280-700 nm, especially preferably at least 350-500 nm, e.g. 370-500 nm or 400-500 nm. Preferably at least one compound in said composition is capable of achieving protection in these wavelength ranges. Protection may be assessed by various techniques, including the time taken to develop a light induced response or the severity of that response, e.g. erythema or burns, e.g. using the currently available tests to determine SPF ratings. When such a test is performed, preferably the composition achieves a SPF of at least 2, preferably at least 10, 20, 30 or 50.

Conveniently however, in order to test efficacy e.g. to filter light of wavelengths that do not significantly result in such responses (e.g. UVA, particularly long-wavelength UVA, i.e. 340-400 nm), in vitro tests may be conducted such as filtering of light through filters (to simulate skin) comprising compounds of interest, or determining the extinction coefficient, to determine the ability of those compounds to absorb radiation. In methods which employ a filter comprising the test compound, the efficacy of absorption may be determined directly or indirectly by assessing the level of radiation (e.g. of a particular wavelength) passing through the filter or by assessing the effect of that radiation passing through a filter with or without the test compound, e.g. on cells which are sensitive to radiation and show a response to such radiation.

Preferably in such tests, (e.g. as described in the Examples), said compounds prevent more than 40%, preferably more than 50 or 600 transmission at a given wave-length. Preferred compounds for use in compositions of the invention preferably exhibit maximal absorption in the 400-500 nm range, e.g. >1.5 to 2 times greater absorption at a given wavelength in the 400-500 nm range compared to absorption at 350 nm.

Appropriate techniques for in vitro analysis involve the application of a test compound to a substrate which preferably simulates skin (e.g. a collagen substrate or a quartz plate with simulated skin topography) which is then irradiated with radiation reflecting full solar radiation or preferably narrower wavelength radiation, e.g. using a Xenon arc to simulate the solar UV spectrum, e.g. 290-400 nm.

The UV absorbance of the test compound may be measured, e.g. using a Labsphere UV-1000S UV transmitter analyzer (Labsphere Inc., North Sutton, N.H.). The ability of the test compound to absorb UVA as assessed by e.g. critical wavelength determination (as described by Diffey et al., 2000, J. Am. Acad. Dermatol., 43(6), p1024-1035) provides an indication of the efficacy of the test compound to absorb in the UV range of the spectrum. Preferably the critical wavelength is more than 360 nm, especially preferably >370 or 380 nm, especially in combination with the SPF values described above.

The invention thus provides a method of treating or preventing the effects of irradiation in a human or non-human animal wherein a pharmaceutical compound or composition as described hereinbefore is administered to said animal. Alternatively stated, the present invention provides the use of a pharmaceutical compound or composition as described herein in the preparation of a medicament for treating or preventing the effects of irradiation of a human or non-human animal body.

In a preferred aspect the invention provides a method of treating or preventing the effects of solar radiation on a human wherein a pharmaceutical compound or composition as described hereinbefore is topically administered to the skin or hair of said human. This method serves to protect the skin or hair from the deleterious effects of said solar radiation.

As used herein, "irradiation" refers to direct or indirect irradiation from one or more natural or synthetic light sources, particularly from the sun, i.e. solar radiation. Preferably said radiation is of light in the range 280-700 nm, especially preferably at least 350-500 nm, e.g. 400-480 nm or 400-500 nm. The "effects" of irradiation may be damaging effects including burns, erythema, premature aging and wrinkling of the skin (dermatoheliosis), development of pre-malignant lesions (solar keratoses) and various malignant tumours or other effects which are undesirable for, for example, cosmetic reasons, e.g. melanin deposition.

As used herein, "treating" refers to the reduction, alleviation or elimination, preferably to normal non-irradiated levels, of one or more of the symptoms or effects of said irradiation e.g. presence or extent of burning or pigmentation, relative to the symptoms or effects present on a different part of the body of said individual not subject to irradiation or in a corresponding individual not subject to irradiation. "Preventing" refers to absolute prevention, or reduction or alleviation of the extent or timing (e.g. delaying) of the onset of that symptom or effect.

The method of treatment or prevention according to the invention may advantageously be combined with administration of one or more active ingredients which are effective in treating or preventing the effects of irradiation. Preferably such additional active ingredients include sunscreen agents (as described herein and as known in the art), antioxidants, vitamins and other ingredients conventionally employed in sunscreen and cosmetic preparations of the art.

Thus, pharmaceutical compositions of the invention may additionally contain one or more of such active ingredients.

According to a yet further aspect of the invention we provide products containing one or more compounds as herein defined and one or more additional active ingredients as a combined preparation for simultaneous, separate or sequential use in human or animal therapy.

The compositions of the invention may be formulated in conventional manner with one or more physiologically acceptable carriers, excipients and/or diluents, according to techniques well known in the art using readily available ingredients. Where appropriate compositions according to the invention are sterilized, e.g. by γ-irradiation, autoclaving or heat sterilization, before or after the addition of a carrier or excipient where that is present, to provide sterile formulations.

Thus, the active ingredient may be incorporated, optionally together with other active substances as a combined prepara-tion, with one or more conventional carriers, diluents and/or excipients, to produce conventional galenic preparations such as tablets, pills, powders, lozenges, sachets, cachets, elixirs, suspensions (as injection or infusion fluids), emulsions, solutions, syrups, aerosols (as a solid or in a liquid medium), ointments, soft and hard gelatin capsules, suppositories, sterile injectable solutions, sterile packaged powders, and the like. Biodegradable polymers (such as polyesters, polyanhydrides, polylactic acid, or polyglycolic acid) may also be used for solid implants. The compositions may be stabilized by use of freeze-drying, undercooling or Permazyme.

Suitable excipients, carriers or diluents are lactose, dextrose, sucrose, sorbitol, mannitol, starches, gum acacia, calcium phosphate, calcium carbonate, calcium lactose, corn starch, alginates, tragacanth, gelatin, calcium silicate, microcrystalline cellulose, polyvinylpyrrolidone, cellulose, water syrup, water, water/ethanol, water/glycol, water/polyethylene, glycol, propylene glycol, methyl cellulose, methylhydroxybenzoates, propyl hydroxybenzoates, talc, magnesium stearate, mineral oil or fatty substances such as hard fat or suitable mixtures thereof. Agents for obtaining sustained release formulations, such as carboxypolymethylene, carboxymethyl cellulose, cellulose acetate phthalate, or polyvinylacetate may also be used.

The compositions may additionally include lubricating agents, wetting agents, emulsifying agents, viscosity increasing agents, granulating agents, disintegrating agents, binding agents, osmotic active agents, suspending agents, preserving agents, sweetening agents, flavouring agents, adsorption enhancers (e.g. surface penetrating agents or for nasal delivery, e.g. bile salts, lecithins, surfactants, fatty acids, chelators), browning agents, organic solvent, antioxidant, stabilizing agents, emollients, silicone, alpha-hydroxy acid, demulcent, anti-foaming agent, moisturizing agent, vitamin, fragrance, ionic or non-ionic thickeners, surfactants, filler, ionic or non-ionic thickener, sequestrate, polymer, propellant, alkalinizing or acidifying agent, opacifier, colouring agents and fatty compounds and the like.

The compositions of the invention may be formulated so as to provide quick, sustained or delayed release of the active ingredient after administration to the body by employing techniques well known in the art.

The composition may be in any appropriate dosage form to allow delivery or for targeting particular cells or tissues, e.g. as an emulsion or in liposomes, niosomes, microspheres, nanoparticles or the like with which the active ingredient may be absorbed, adsorbed, incorporated or bound. This can effectively convert the product to an insoluble form. These particulate forms may overcome both stability (e.g. degradation) and delivery problems.

These particles may carry appropriate surface molecules to improve circulation time (e.g. serum components, surfactants, polyoxamine908, PEG etc.) or moieties for site-specific targeting, such as ligands to particular cell borne receptors. Appropriate techniques for drug delivery and for targeting are well known in the art and are described in WO99/62315.

The use of solutions, suspensions, gels and emulsions are preferred, e.g. the active ingredient may be carried in water, a gas, a water-based liquid, an oil, a gel, an emulsion, an oil-in water or water-in-oil emulsions a dispersion or a mixture thereof.

Compositions may be for topical (e.g. to the skin or hair), oral or parenteral administration, e.g. by injection. Topical compositions and administration are however preferred, and include gels, creams, ointments, sprays, lotions, salves, sticks, soaps, powders, films, aerosols, drops, foams, solutions, emulsions, suspensions, dispersions e.g. non-ionic vesicle dispersions, milks and any other conventional pharmaceutical forms in the art.

Ointments, gels and creams may, for example, be formulated with an aqueous or oily base with the addition of suitable thickening and/or gelling agents. Lotions may be formulated with an aqueous or oily base and will, in general, also contain one or more emulsifying, dispersing, suspending, thickening or colouring agents. Powders may be formed with the aid of any suitable powder base. Drops and solutions may be formulated with an aqueous or non-aqueous base also comprising one or more dispersing, solubilising or suspending agents. Aerosol sprays are conveniently delivered from pressurised packs, with the use of a suitable propellant.

Alternatively, the compositions may be provided in a form adapted for oral or parenteral administration. Alternative pharmaceutical forms thus include plain or coated tablets, capsules, suspensions and solutions containing the active component optionally together with one or more inert conventional carriers and/or diluents, e.g. with corn starch, lactose, sucrose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof.

The concentration of active ingredient in compositions of the invention, depends upon the nature of the compound used, the mode of administration, the course of treatment, the age and weight of the patient, the cosmetic or medical indication, the body or body area to be treated and may be varied or adjusted according to choice. Generally however, concentration ranges for the compound described herein is 0.0005, 0.001 or 0.01 to 25%, e.g. 0.01 to 10%, such as 0.1 to 5, e.g. 1-5% (w/w of the final preparation for administration, particularly for topical administration). Said concentrations are determined by reference to the amount of the compound itself and thus appropriate allowances should be made to take into account the purity of the composition. Effective single doses may lie in the range of from 1-100 mg/day, preferably 2-10 mg/day, depending on the animal being treated, taken as a single dose.

The administration may be by any suitable method known in the medicinal arts, including for example oral, parenteral (e.g. intramuscular, subcutaneous, intraperitoneal or intravenous) percutaneous, buccal, rectal or topical administration or administration by inhalation. The preferred administration forms will be administered orally, or most preferably topically. As will be appreciated oral administration has its limitations if the active ingredient is digestible. To overcome such problems, ingredients may be stabilized as mentioned previously.

Administration may be conducted before, during or after irradiation to offer prevention or treatment of the effects of irradiation. Thus for example the composition may be administered orally or applied topically up to e.g. 1 day, but preferably less than 1 hour before irradiation, at any time during irradiation and post-irradiation, e.g. in the 12 hours post-irradiation.

Sunscreen formulations may be presented as topical formulations as described hereinbefore, particularly as body, face or lip milks, foams, sprays, lotions, gels or balms. Depending on their formulation and the compound used in the composition, sunscreen preparations of the invention may also have cosmetic properties, e.g. by the inclusion of additional components or the selection of a coloured compound of the invention. Similarly, cosmetic preparations as described herein may have sunscreen properties.

The present invention also extends to particular cosmetic compositions or preparations (personal care products) comprising the compositions described hereinbefore. Such preparations may take the form of make-up products (such as eye or face products, including eye shadow, powder, lipstick, foundation, mascara, blush, eyeliner, nail polish, tinted creams and foundations, sun make-up), creams, lotions or colourants. Preferably such preparations are in the form of an anhydrous or aqueous solid or paste. The carotenoids of the invention may be used to impart colour, sunscreen and/or antioxidant properties to such preparations. For sunscreen products, the compositions may be as described hereinbefore particularly for topical administration to the skin. For the treatment or protection of hair, the composition may be in the form of a hair rinse, spray mist, gel, mousse, shampoo, conditioner, lotion, emulsion or colouring product.

The invention thus further extends to a method of preparing the above described sunscreen or cosmetic preparation comprising adding a compound or composition as described hereinbefore to a pharmaceutically acceptable diluent, carrier and/or excipient or base sunscreen or cosmetic, wherein the base sunscreen or cosmetic may comprise ingredients which impart photoprotective and/or cosmetic, e.g. colouring, properties. The use of compounds or composition of the invention to prepare such cosmetics/sunscreens is also considered an object of the invention.

Animals to which the compositions may be applied or administered include mammals, reptiles, birds, insects and fish which suffer deleterious effects from light irradiation. Preferably the animals to which the compositions of the invention are applied are mammals, particularly primates, domestic animals, livestock and laboratory animals. Thus preferred animals include mice, rats, rabbits, guinea pigs, cats, dogs, monkeys, pigs, cows, goats, sheep and horses. Especially preferably the compositions are applied or administered to humans.

"Body coverings" or "body surfaces" to which the compositions of the invention may be applied include body coverings such as skin, bodily outgrowths such as hair and nails and surfaces such as mucosal membranes, but also include equivalents in other animals such as scales or feathers.

The following Examples are given by way of illustration only in which the Figures referred to are as follows.

EXAMPLE 1

Formulations

Exemplary formulations in accordance with the invention are as follows:

Sunscreens
Body lotions

| | % w/w |
|---|---|
| FORMULATION 1 | |
| Lanolin | 4.5 |
| Cocoa butter | 2.0 |
| Glyceryl stearate | 3.0 |
| Stearic acid | 2.0 |
| Octyl dimethyl PABA (UVB filter, optional) | 7.0 |
| Benzophenone-3 (UVB filter, optional) | 3.0 |
| Propylparaben | 0.1 |
| Methylparaben | 0.3 |
| Triethanolamine | 1.0 |
| Sorbitol | 5.0 |
| Carotenoid of the invention | 1.0-5.0 |
| Water | qs to 100 |
| FORMULATION 2 | |
| Phase A | |
| Isopropyl myristate | 4.0 |
| Mineral oil | 6.5 |
| Grape seed oil | 2.5 |
| Stearyl alcohol | 2.0 |
| Petrolatum | 2.0 |
| Octyl methoxycinnamate (UVB filter - optional) | 5.0 |
| Carotenoid of the invention | 1.0-5.0 |
| Phase B | |
| Sorbitan stearate | 6.0 |
| Disodium ricinoleamido MEA-sulfosuccinate | 0.2 |
| Glycerine | 4.0 |
| Allantoin | 0.2 |
| d-Panthenol | 0.8 |
| titanium oxide and water (optional) | 15.0 |
| Water | qs to 100 (phase A&B) |
| Phase C | |
| Preservative | qs |

Produced by separately heating phases A and B to 80° C., then adding A to b, stirring intensively. After homogenizing the mixture is allowed to cool to 25° C. with slow agitation after which phase C is added.

Hair products

| | % w/w |
|---|---|
| SHAMPOO | |
| Anionic surfactant | 2.5-1.5 active |
| Amphoteric surfactant | 0-4 active |
| Alkanolamide | 0-5 |
| Polymeric/associative thickener | 0-5 |
| Carotenoid of the invention | 1-5 |
| UVA/B filters (e.g octyl methoxy cinnamate, avobenzone or oxybenzone) - optional | 1-10 |
| Preservative | qs |
| Fragrance | qs |
| pH adjuster | qs |
| Electrolyte | qs |
| Water | qs to 100 |
| HAIRSPRAY | |
| Resin plasticizer | 0-2 |
| Film forming resin | 2-8 |
| Ethanol | 0-70 |
| Alkanolamine or alternative neutralizing agent | 0-4 |
| Carotenoid of the invention | 1-5 |
| UVA/B filters (e.g octyl methoxy cinnamate, avobenzone or oxybenzone) - optional | 1-10 |
| Preservative | qs |
| Fragrance | qs |
| Hydrocarbon or alternative propellant | 10-40 |
| Water | qs to 100 |

EXAMPLE 2

Extraction Protocols

Diadinoxanthin Extraction (from Micro Algae):

Extraction is performed in a nitrogen atmosphere in equipment covered with aluminium foil.

1. The pH of a water suspension of the microalgae *P. tricornutum* (14 g dry weight per liter of water) was adjusted to 8.3 and ethanol was added to a final ratio of water:ethanol=0.3:1.0.
2. The water-ethanol solution was extracted by mixing with heptane (water-ethanol solution:heptane=1.3:1.0) for 1 hour at 20° C.
3. The solution was separated into three phases by centrifugation (10 minutes at 3222×g): An upper heptane phase enriched in diadinoxanthin and fucoxanthin, a lower ethanol-water phase enriched in chlorophylls and degradation products of chlorophylls, and a third mid-phase with precipitated materials. The ratio of the concentration of diadinoxanthin to fucoxanthin in the water-ethanol phase was approximately 1:6.
4. Water was added to the water-ethanol phase until a water:ethanol ratio of 0.7:1.0 was reached. This solution was extracted by a similar amount of heptane and the phases separated by centrifugation (as in step 3). Diadinoxanthin was enriched in the heptane phase (diadinoxanthin:fucoxanthin=1:1), and fucoxanthin and fucoxanthin-derivatives in the ethanol-water phase.
5. The heptane phase was stored overnight at −20° C. to separate fucoxanthin which was separated by centrifugation as described above. (Alternatively, the precipitated material may be removed with a pipette.)
6. The heptane phase was used for further purification of diadinoxanthin by HPLC as described hereinbefore to yield 60-70w of the diadinoxanthin found in the starting material.

Optimization

Various parameters in the above described basic method were varied to establish the effect of water concentration, pH and temperature on the isolation method. The results are provided in the table below.

1. Altering the Water Concentration

The table below shows the phase distribution (in %) of the carotenoids using different water levels. The method was performed at room temperature without pH adjustment.

| Extraction with | | | | | | |
|---|---|---|---|---|---|---|
| Water | EtOH | Heptane | Phase | Diadino | Fuco | Chla |
| 0 | 1 | 1 | water-EtOH | 88 | 93 | 55 |
| 0.1 | 1 | 1 | water-EtOH | 7 | 51 | 0 |
| 0.2 | 1 | 1 | water-EtOH | 94 | 98 | 7 |
| 0.4 | 1 | 1 | water-EtOH | 78 | 97 | 0 |
| 0 | 1 | 1 | heptane | 12 | 7 | 45 |
| 0.1 | 1 | 1 | heptane | 93 | 49 | 100 |
| 0.2 | 1 | 1 | heptane | 6 | 2 | 93 |
| 0.4 | 1 | 1 | heptane | 22 | 3 | 100 |

2. Temperature/pH Effects

The table below shows the effects of temperature and pH on the separation of diadinoxanthin from fucoxanthin by extraction of the water:ethanol phase (1:1) with heptane after extraction of Chl a with heptane. Values indicated are for the amount of each compound in the indicated phase. The value in brackets indicates the % distribution between the two phases.

| | Water-EtOH phase | | Heptane phase | |
|---|---|---|---|---|
| Buffer | Diadino | Fuco | Diadino | Fuco |
| Phosphate, pH 11, 20° C. | 0 (0%) | 260 (5%) | 1500 (100%) | 4860 (95%) |
| Phosphate, pH 11, 50° C. | 0 (0%) | 135 (5%) | 1470 (100%) | 2745 (95%) |
| NaOH-buffer, pH 12.2, 50° C. | 0 (0%) | 0 (0%) | 1440 (100%) | 0 (0%) |

Recovery:

| | Total present in both phases | | % recovery of initial amount | |
|---|---|---|---|---|
| Buffer | Diadino | Fuco | Diadino | Fuco |
| Phosphate, pH 11, 20° C. | 1500 | 5120 | 106% | 81% |
| Phosphate, pH 11, 50° C. | 1470 | 2880 | 104% | 46% |
| NaOH-buffer, pH 12.2, 50° C. | 1440 | 0 | 102% | 0% |

This shows that diadinoxanthin is stable under the conditions used whereas fucoxanthin is more sensitive to extreme temperatures and pH.

3. Temperature Effects

The table below shows the effects of temperature on extraction for 200 minutes at a ratio of water:ethanol:heptane of 1:1:1 at pH 11.

| Temp | Water-EtOH phase | | | Heptane phase | | |
|---|---|---|---|---|---|---|
| (° c.) | Diadino | Fuco | Chl a | Diadino | Fuco | Chl a |
| 20 | 170 | 380 | 0 | 1155 | 1065 | 3290 |
| 35 | 180 | 210 | 0 | 1260 | 610 | 3505 |
| 50 | 190 | 0 | 0 | 1310 | 95 | 4010 |

Diadinoxanthin is thus stable at various temperatures whereas fucoxanthin was more sensitive to higher temperatures.

Fucoxanthin Extraction (from Macro Algae):

This method is a modification of the method (above) for diadinoxanthin.

1. Fronds and stripes (from the algae *Laminaria hyperborea*) were cut in pieces.
2. Ethanol (5 ml) and heptane (5 ml) were added to the algae material (1 g, wet weight), mixed in a Whirl-mixer (3×15s) and placed at 4° C., for 4 hours. (In some protocols, at this stage the mixture was centrifuged and the carotenoid extracted from the ethanol or heptane fraction. In other protocols methane was in used instead of ethanol.)
3. 1.5 ml water was added and mixed in a Whirl-mixer (3×15 s) and placed at 4° C. for 1 hour. The solution was centrifuged (10 minutes at 3222×g) and the ethanol-water phase was used for further purification of fucoxanthin. (Purification was performed by HPLC as described hereinbefore.)
4. A yield of 800 μg/g (dry weight) was observed.

The method provides an extraction method for large scale extraction of fucoxanthin while at the same time removing other cell constituents that are regarded as difficult to separate from carotenoids (for example chlorophyll a) from the sample.

EXAMPLE 3

Efficacy of Irradiation Absorption Using an In Vitro Skin Model

Method

The in vitro method of Springsteen was used (Springsteen et al., 1999, Analytica Chimica Acta, 380, p155-164). Vitroskin was used as the skin simulator and Miglyol (Miglyol 812F Neutraloel CHG. 040906) was used as the solvent. The tests were performed with a Varian Cary 300 Conc UV-Visible Spectrophotometer (with an integrating sphere). Fucoxanthin and diadinoxanthin (isolated as described in Example 2) were tested at the concentrations indicated on FIG. 3.

Results

Figure 3:
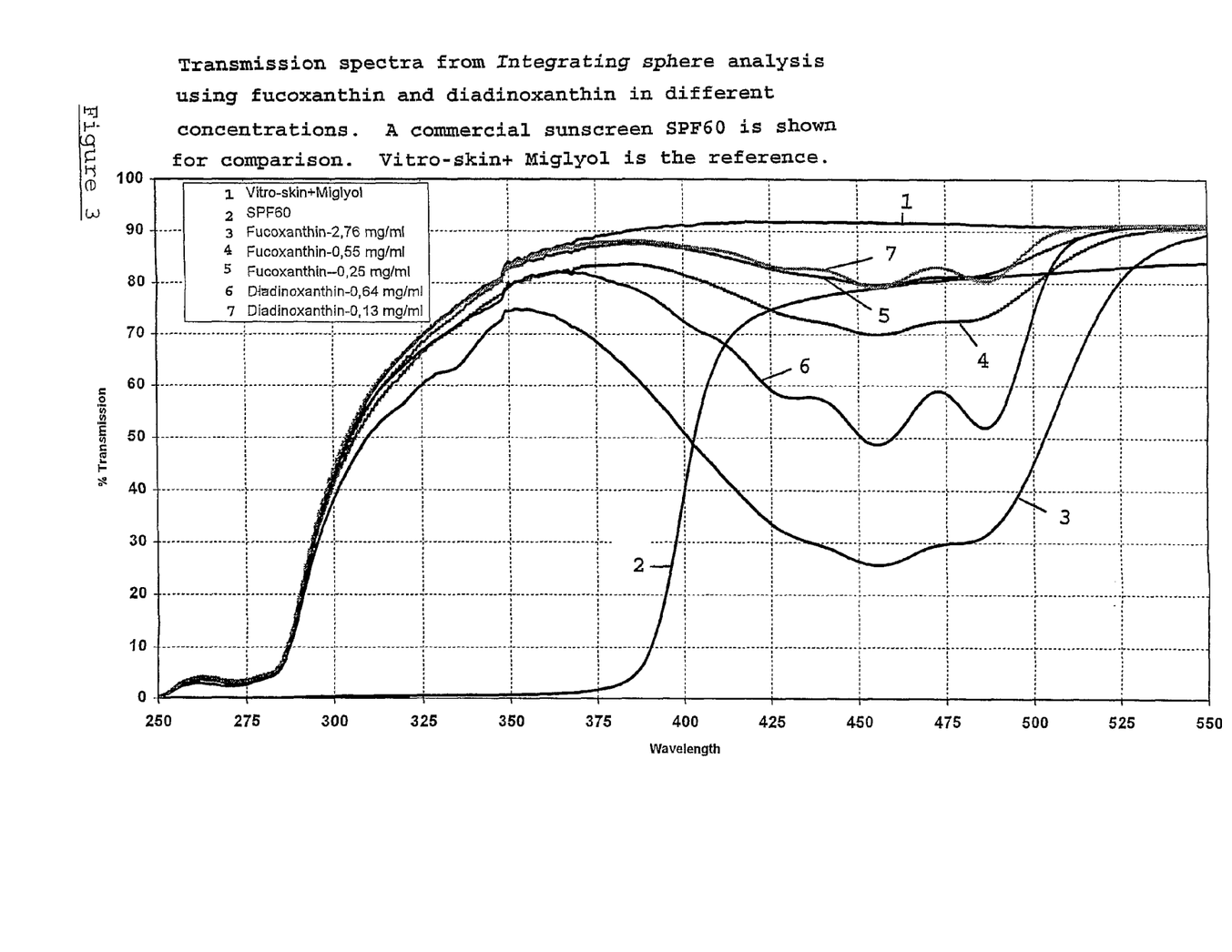
FIG. 3 shows the transmission spectra from Integrating sphere analysis using fucoxanthin and diadinoxanthin at different concentrations. A commercial sunscreen SPF60 was used for comparison. Vitro–skin+miglyol was used as the control. Curve 1: Vitro–skin+Miglyol, 2: SPF60, 3:fucoxanthin at 2.76 mg/ml, 4:fucoxanthin at 0.55 mg/ml, 5:fucoxanthin at 0.25 mg/ml, 6:diadinoxanthin at 0.64 mg/ml, 7:diadinoxanthin at 0.13 mg/ml.
Figure 4:
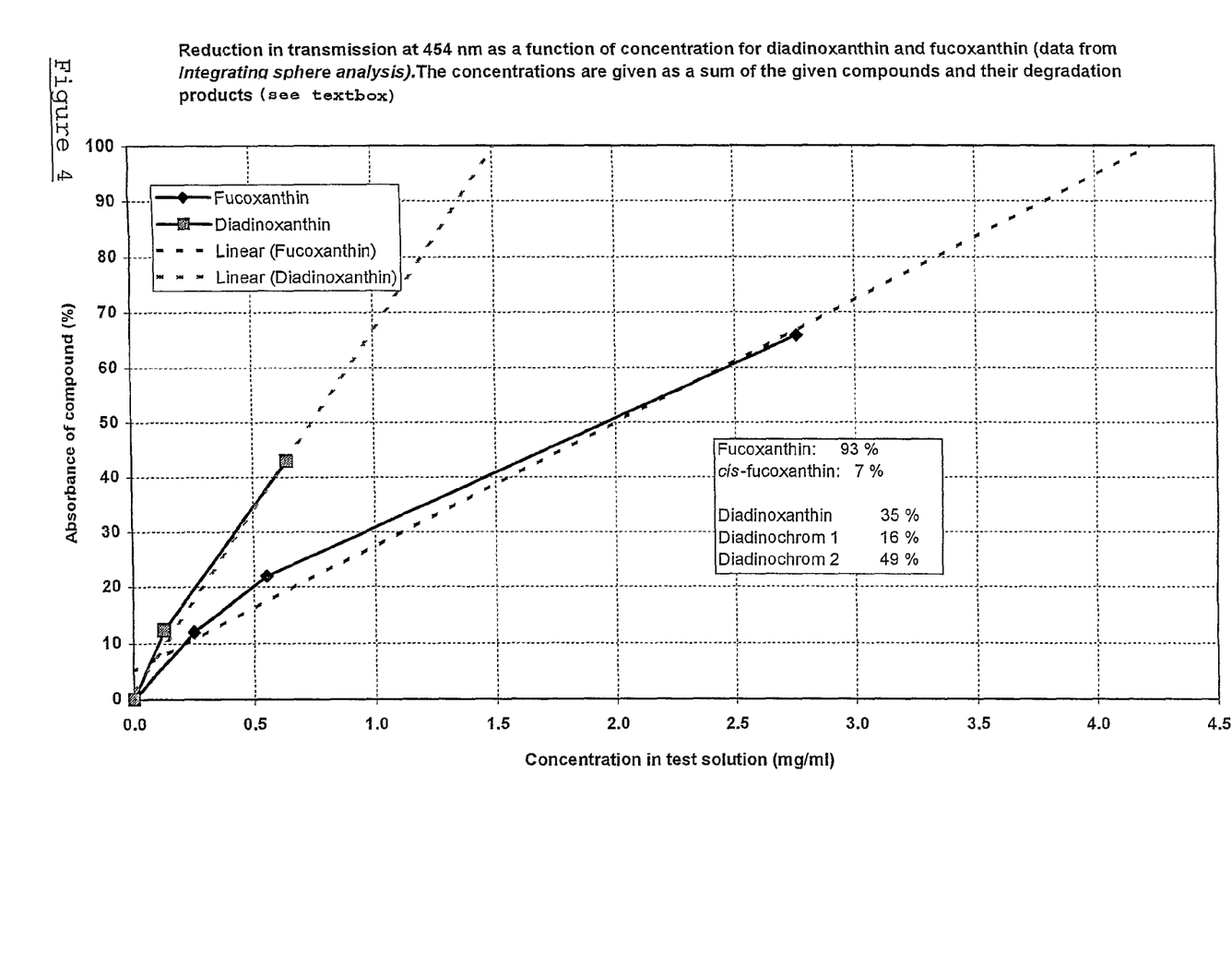
FIG. 4 shows the reduction in transmission at 454 nm as a function of concentration for diadinoxanthin and fucoxanthin (data from Integrating Sphere analysis). The concentrations are given as the sum of the given compounds and their degradation products (cis-fucoxanthin and diadinochrome). Solid lines with squares—diadinoxanthin. Solid line with diamonds—fucoxanthin. Dashed lines illustrate a projected linear relationship.

The results for diadinoxanthin and fucoxanthin (at different concentrations) are shown in FIG. 3. The results were compared to a conventional SPF 60 sun lotion, and demonstrates the compounds, ability to absorb irradiation, particularly in the blue light range of the spectrum, but also in the upper UVA area. FIG. 4 shows the transmission in % plotted against the wavelength of the light. The dashed lines display roughly the relation between concentration and absorption and indicates that less than 5 mg/ml would be sufficient in the final solution to provide sufficient protection at 454 nm (blue light).

The invention claimed is:

1. A method of treating or protecting against the effects of irradiation in a human or non-human animal wherein a photoprotective composition comprising from 0.0005% to 25% w/w of a carotenoid compound, said carotenoid compound comprising diadinoxanthin or a pharmaceutically acceptable salt thereof, together with one or more pharmaceutically acceptable excipients and/or diluents, is topically administered to said human or non-human animal.

2. A method as claimed in claim 1 wherein said carotenoid compound used in said composition is purified to a degree of purity of more than 30%.

3. A method as claimed in claim 1 wherein said carotenoid compound is obtained or derived from naturally occurring sources.

4. A method as claimed in claim 1 wherein said carotenoid compound is isolated from microalgae belonging to the phytoplankton classes Diatoms, Dinoflagellates, Prymnesiophytes, Euglenophytes and Chrysophytes.

5. A method as claimed in claim 1 wherein said carotenoid compound is generated synthetically.

6. A method as claimed in claim 1 wherein said carotenoid compound is combined in the composition with one or more additional sunscreen compounds.

7. A method as claimed in claim 6 wherein said composition contains two or more carotenoid compounds.

8. A method as claimed in claim 1 wherein said composition is in the form of a solution, suspension, gel, emulsion, ointment or cream.

9. A method as claimed in claim 1 wherein said composition optionally comprises one or more additional sunscreen compounds wherein said composition is in the form of a gel, emulsion, ointment or cream.

10. A method as claimed in claim 1 wherein said composition is suitable for topical administration.

11. A method as claimed in claim 1 wherein said composition is formulated in a make-up product, a body product or a hair product and optionally comprises one or more additional sunscreen compounds.

12. A method as claimed in claim 1 wherein said composition is administered in combination with one or more active ingredients which are effective in treating or preventing the effects of radiation.

13. A method as claimed in claim 1 wherein said composition is topically administered to the skin or hair of a human.

14. A method as claimed in claim 1 wherein said composition is photoprotective against light irradiation with a wavelength of 400-500 nm.

15. A photoprotective composition comprising from 0.0005% to 25% w/w of a carotenoid and one or more sunscreen compounds, wherein said carotenoid is diadinoxanthin, or a pharmaceutically acceptable salt thereof, together with one or more pharmaceutically acceptable excipients and/or diluents.

16. A photoprotective composition as claimed in claim 15 for use as a medicament.

17. A method of treating or protecting against the effects of irradiation in a human or non-human animal comprising topically administering to the human or non-human animal the photoprotective composition as defined in claim 15.

18. A method of preparing a photoprotective or photoprotected product comprising incorporating the photoprotective composition defined in claim 15 into said product, or impregnating said product with said composition.

19. A photoprotective or photoprotected product obtainable by the method of claim 18.

20. A method of purifying a carotenoid as defined in the composition of claim 15 from algae comprising the steps of
  (i) mixing algae with water adjusted to a pH of 8 to 12,
  (ii) adding alcohol to a final water:alcohol ratio of 0.2 to 1.5:1.0,
  (iii) extracting said alcohol-water mixture (aqueous phase) with a liquid organic solvent (organic phase) at a water-alcohol:organic solvent ratio of 0.75 to 1.5:1.0,
  (iv) optionally cooling said organic phase at less than 10° C. for more than 5 minutes; and
  (v) collecting the aqueous and/or organic phase and purifying the carotenoid therefrom.

21. A method as claimed in claim 20 wherein said alcohol is ethanol and said organic solvent is heptane.

* * * * *